United States Patent [19]

Leon et al.

[11] Patent Number: 5,403,252
[45] Date of Patent: Apr. 4, 1995

[54] EXERCISE APPARATUS AND METHOD FOR SIMULATING HILL CLIMBING

[75] Inventors: Tomas F. Leon, Chicago; Robert L. Hood, Grayslake; Robert E. Quast, Kildeer; David J. Thum, Roselle; Emil S. Golen, Barrington, all of Ill.

[73] Assignee: Life Fitness, Franklin Park, Ill.

[21] Appl. No.: 971,422

[22] Filed: Nov. 3, 1992

Related U.S. Application Data

[63] Continuation-in-part of Ser. No. 881,918, May 12, 1992, Pat. No. 5,318,487.

[51] Int. Cl.$^6$ ............................................. A63B 21/005
[52] U.S. Cl. ......................................... 482/5; 482/52; 482/902; 482/903; 73/379.01
[58] Field of Search ................................. 482/1, 3–9, 482/51–54, 57–62, 111–113, 900–903; 128/25 R, 25 B; 73/379.01, 379.06, 379.07; 364/413.04, 550; 340/762, 765, 782, 784

[56] References Cited

U.S. PATENT DOCUMENTS

| | | |
|---|---|---|
| 3,497,215 | 2/1970 | Harrison et al. . |
| 3,529,474 | 9/1970 | Olson et al. . |
| 3,628,791 | 12/1971 | Garcia . |
| 3,784,194 | 1/1974 | Perrine ............................ 482/113 |
| 3,845,756 | 11/1974 | Olsson .............................. 482/62 X |
| 3,970,302 | 7/1976 | McFee . |
| 4,082,267 | 4/1978 | Flavell . |
| 4,358,105 | 11/1982 | Sweeney et al. ............... 482/901 X |
| 4,496,147 | 1/1985 | DeCloux et al. . |
| 4,600,187 | 7/1986 | Schenker . |
| 4,676,501 | 6/1987 | Hoagland et al. . |
| 4,685,669 | 8/1987 | DeCloux . |
| 4,687,195 | 8/1987 | Potts . |
| 4,708,338 | 11/1987 | Potts . |
| 4,720,093 | 1/1988 | Del Mar . |
| 4,735,410 | 4/1988 | Nobuta .......................... 482/902 X |
| 4,790,528 | 12/1988 | Nakao et al. .................... 482/902 X |
| 4,938,474 | 7/1990 | Sweeney et al. . |
| 4,938,475 | 7/1990 | Sargeant et al. ............... 482/901 X |
| 5,013,031 | 5/1991 | Bull . |
| 5,033,733 | 7/1991 | Findlay . |
| 5,067,710 | 11/1991 | Watterson et al. ................ 482/5 X |
| 5,135,447 | 8/1992 | Robards, Jr. et al. . |
| 5,149,084 | 9/1992 | Dalebout et al. ................ 482/52 X |
| 5,207,621 | 5/1993 | Koch et al. ..................... 482/902 X |

Primary Examiner—Joe H. Cheng
Attorney, Agent, or Firm—Michael B. McMurry

[57] ABSTRACT

A climbing exercise apparatus is provided having a frame on which two pedals are pivotally mounted to provide a user with a vertically reciprocating exercise movement, and a control panel for user input and output. A dynamic break, alternator or the like applies a variable level of resistance (via a suitable transmission) against the user's movement. The resistance varies over time in accordance with a control signal generated by a computer. The value of the control signal is independent of the rate at which the user steps. A display successively displays images of hills. Each hill is associated with one of the series of values, and that value is graphically represented as part of or in visual association with the hill image.

21 Claims, 5 Drawing Sheets

EXERCISE APPARATUS AND METHOD FOR SIMULATING HILL CLIMBING

RELATED APPLICATIONS

This application is a continuation in-part of U.S. patent application Ser. No. 07/881,918, filed on May 12, 1992 (Attorney Docket No. 31720-20436), now U.S. Pat. No. 5,318,487.

FIELD OF THE INVENTION

The invention relates to exercise equipment, and in particular to equipment for simulating aerobic stair climbing exercise.

BACKGROUND OF THE INVENTION

Stair climbing is recognized as a particularly effective type of aerobic exercise, and as a result, exercise machines facilitating this type of exercise are becoming increasingly popular.

There have been a variety of approaches taken in designing stair climbing apparatus, including the simulation of an actual staircase as illustrated in U.S. Pat. Nos. 3,497,215 and 4,687,195. Another approach has been to simulate the action of stair climbing by using a pair of reciprocating pedals.

An example of the later approach is described in U.S. Pat. No. 5,135,447 issued to Robards, Jr. et al. on Aug. 4, 1992 (the disclosure of which is hereby incorporated by reference in its entirety). Other examples of this type of machine are described in U.S. Pat. Nos. 3,316,819, 3,529,474, 3,628,791, 3,979,302, 4,496,147, 4,600,187, 4,676,501, and 4,720,093.

As exemplified by U.S. Pat. No. 5,135,447, these machines includes a pair of pedals which are adapted for vertical reciprocating motion to provide a user who is standing on the pedals with a simulated climbing exercise. The vertical reciprocating motion is typically translated into a rotary motion by a suitable system of belts, gears and clutches, for example.

The rotary motion (which may be imparted to a shaft, flywheel or the like) is opposed by a variable source of resistance force, typically an alternator, eddy current break or the like. The alternator is responsive to a control signal for selectively varying the level of resistance. When the user's rate of exercise reaches a predetermined threshold, the control signal causes the resistance to sharply increase. The higher resistance compels the user to decrease his or her rate of exercise. In this manner, variable resistance devices such as alternators have been used to control the rate of user exercise. The rate of user exercise is also controlled by prompting the user to pedal faster or slower. Consequently, variations in exercise intensity are achieved by varying the rate at which the user steps.

In general, the objective of these systems is to simulate stair climbing. Stair climbing is characterized by its uniform, repetitive nature. Ideally, stair climbing apparatus would provide a more dynamic climbing simulation to increase user interest.

SUMMARY OF THE INVENTION

It is therefore an object of the present invention to provide an exercise apparatus for dynamically simulating hill climbing exercise.

In accordance with the invention, a climbing exercise apparatus is provided having a frame on which two pedals are pivotally mounted to provide a user with a vertically reciprocating exercise movement, and a control panel for user input and output. A dynamic break, alternator or the like applies a variable level of resistance (via a suitable transmission) against the user's movement. The resistance automatically varies over time in accordance with a load control signal generated by a computer. The value of the control signal is independent of the rate at which the user steps.

In the preferred embodiment, a computer or other control circuit successively selects a series of difficulty values which correspond to hill heights, sizes, grades or like measures of difficulty. A primary display successively displays images of hills. Each displayed hill image is associated with the currently selected one of the series of difficulty values and that value is graphically represented as part of or in visual association with the hill image.

For example, in the preferred embodiment, an LED display depicts successive hills by lighting a vertical column of LEDs. The value or "height" of the hill is represented by the number of LEDs that are illuminated in the column. Alternatively, more sophisticated representations may be employed, including video depictions of hills.

As each hill is displayed, a load control circuit generates a control signal to vary the load resistance against the user as a function of the displayed hill's difficulty value. In this manner, the exercise movement gets more difficult as the hills depicted by the primary display appear "higher".

In the load preferred embodiment, the control signal is a pulse train. Each pulse is generated at regular intervals of approximately 50 milliseconds. The width (or "duty cycle") of each pulse, however, is modulated by the computer, to effectively control the resistance load imparted by the alternator against the user's movement.

The apparatus may also include a keypad or the like for entering data such as the user's weight and/or an effort level that is selected from a predetermined range. In accordance with one aspect of the invention, the duty cycle of the control signal is modulated as a function of the displayed hill's difficulty value, the square of the user's weight and the user-entered effort level.

DETAILED DESCRIPTION OF THE PREFERRED EMBODIMENT

Technical Environment

Figure 1:
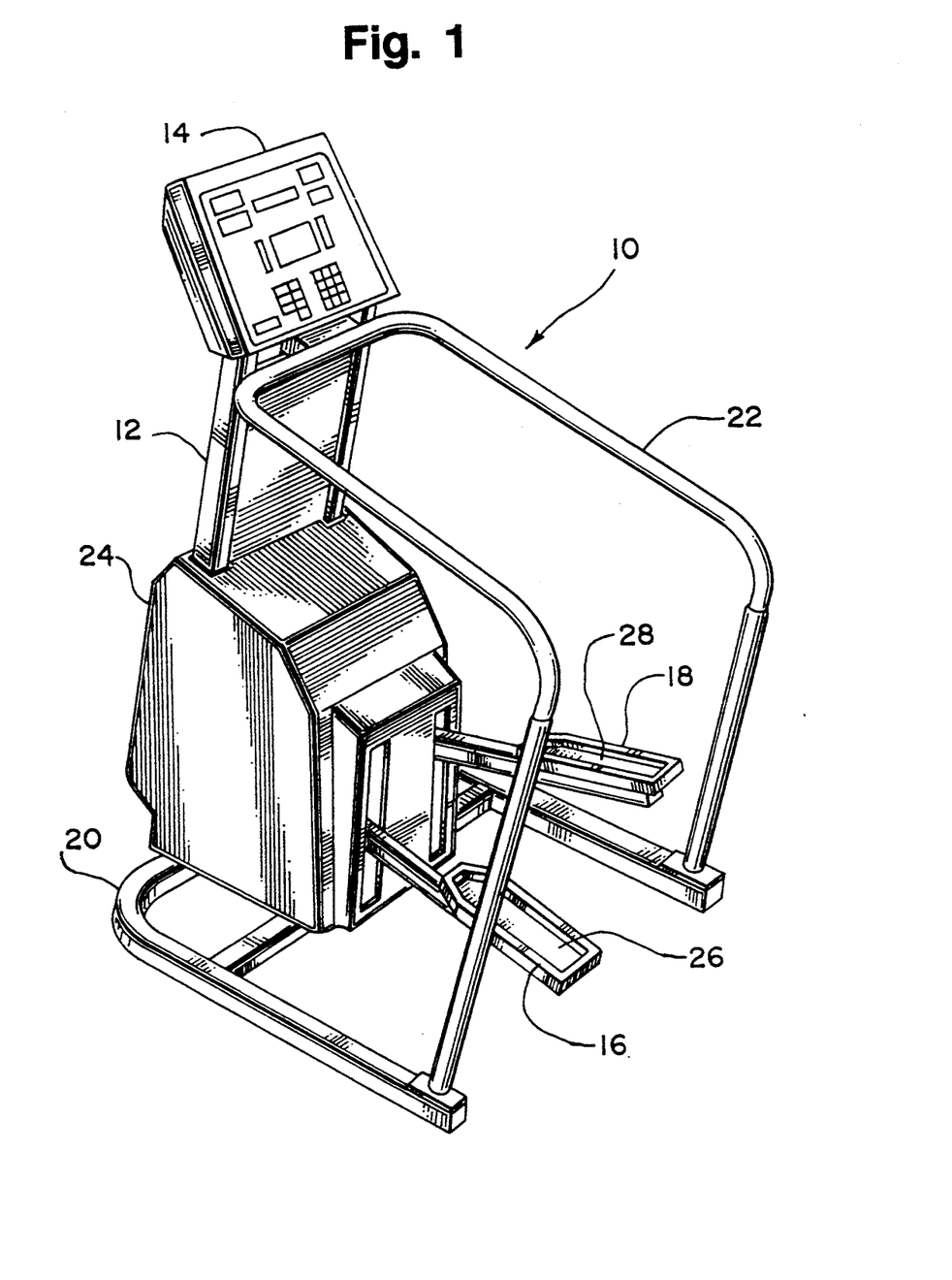
FIG. 1 is a perspective view of a climbing-type exercise device in accordance with the invention.

FIG. 1 shows a climbing-type exercise apparatus 10 that includes a frame 12, a control panel 14, and a pair of pedals 16 and 18. The frame 12 may be of any suitable construction. In the illustrated embodiment, the frame 12 includes a base 20, a tubular section 22, which can be used as a handrail, and a housing 24. The pedals 16 and 18 each include pads 26 and 28, respectively, which form the tread portion of a simulated staircase or hill.

Figure 2:
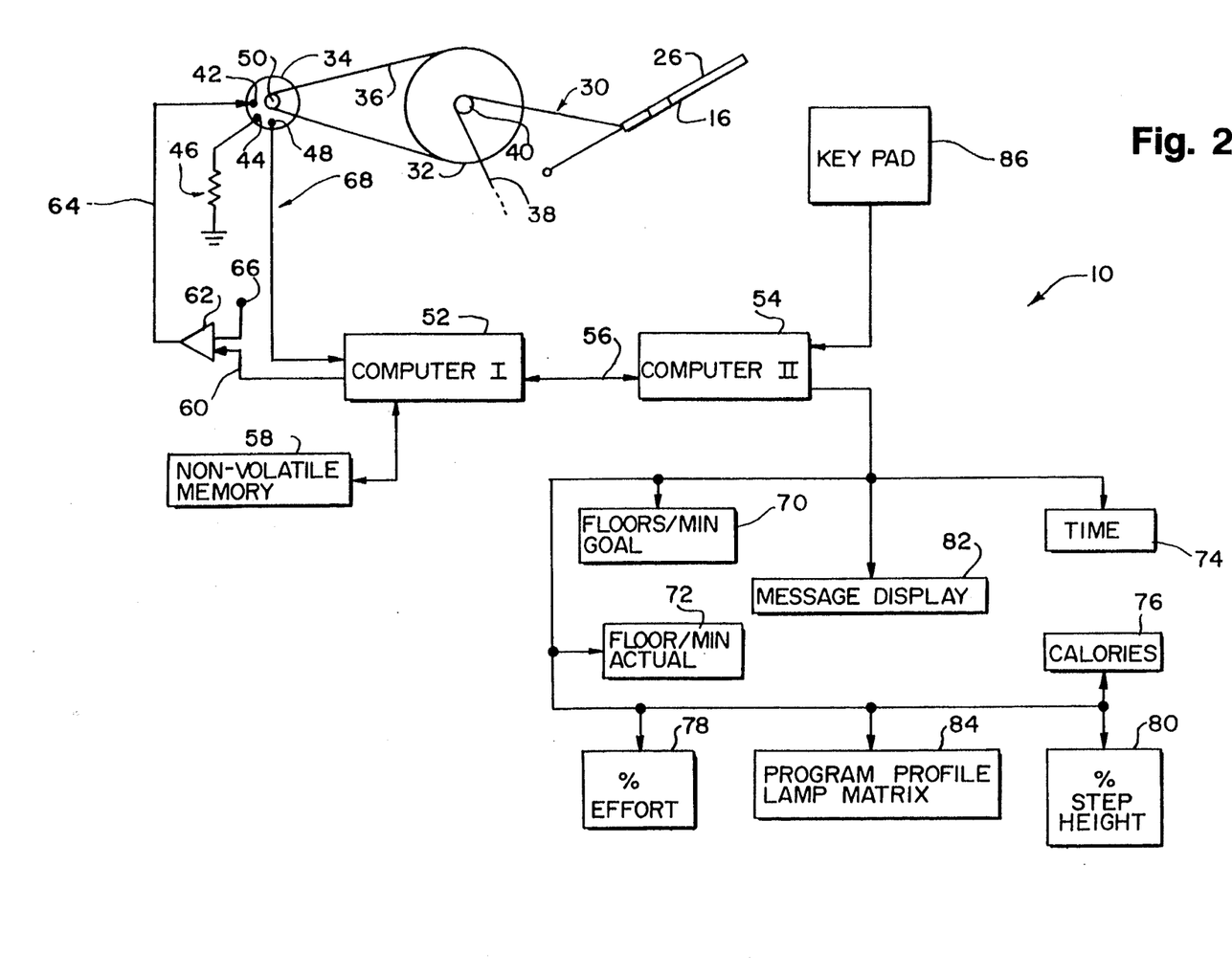
FIG. 2 is a block diagram of the exercise device shown in FIG. 1.

Pedals 16 and 18 are pivotally mounted to the base 20 to allow the user to vertically reciprocate pads 26 and 28 in an exercise motion. As best seen in FIG. 2, a suitable transmission device 30 is disposed in the housing 24 and converts the vertical reciprocating motion of the pedals 16 and 18 into a rotary motion of a flywheel 32. The rotary motion of the flywheel 32 is resisted by an alternator 34, which is coupled to the flywheel 32 by a suitable belt 36.

Transmission device includes a length of the chain 38, which cross connects the pedals 16 and 18. Only a portion of the chain 38 is illustrated in FIG. 2. The chain 38 drivingly engages a pair of sprockets 40 which are coaxially mounted on opposing sides of the flywheel 32. For clarity, only one of the sprockets 40 is illustrated in FIG. 2. One-way clutches (not illustrated) are coupled to each of the sprockets 40 so that the flywheel 32 rotates in only one direction, notwithstanding the fact that the sprockets 40 will rotate bidirectionally due to the reciprocating motion of the chain 38. The invention may be practiced with other suitable transmission devices.

The alternator 34 is a commercially available alternator such as commonly used in automotive applications, and includes a field coil terminal 42, a driven coil terminal 44 that is connected to ground via a 0.5 ohm load resistor 46, and a tap terminal 48. The alternator 34 also includes a rotatable shaft 50 which is driven by the belt 36. As the user vertically reciprocates pedals 16 and 18, he or she drives flywheel 32, which in turn drives alternator shaft 50. The rotation of shaft 50 causes alternator 34 to generate a voltage potential at driven coil terminal 44. The resulting current flows through the resistor 46, thereby dissipating the user's kinetic energy in the form of heat. The resistance force or "load" in opposition to the rotation of shaft 42 (and, consequently, to the user's reciprocating exercise movement) is governed by the current flowing through field coil terminal 42.

The operation of exercise device 10 is controlled by a pair of computers 52 and 54, which are coupled together via a serial communication link 56. Each of computers 52 and 54 includes dynamic memory and input-output interface circuitry, and computer 48 also includes non-volatile memory 58. Computer 52 controls the load resistance of alternator 34, and is preferably a Motorola ™ 68HC05 microcontroller. Computer 52 also calculates the rate of user exercise, the calories consumed, and other exercise related data. Computer 54 manages user input and output via panel 14, and is preferably a Motorola ™ 68HC05 microcontroller. Alternatively, a single, integrated computer can be used.

Computer 52 generates as output a load control signal 60, which is amplified by an amplifier 62. The output 64 of amplifier 62 is coupled to the field coil terminal 42, and the input of amplifier 62 not connected to control signal 60 is tied to a fixed voltage source 66.

Control signal 60 is a pulse train. The pulses are generated at regular intervals of approximately 50 milliseconds. The duration (or "duty cycle") of each pulse, however, is varied by computer 52 to modulate the effective current level through field coil terminal 42.

It will be seen that computer 52 can control the load resistance by modulating the duty cycle of the load control signal 60. Specifically, a greater duty cycle increases the effective current through field current terminal 42, and causes alternator 34 to impart greater load resistance in opposition to the rotation of shaft 40 (and, consequently, to the user's reciprocating exercise movement). In the preferred embodiment, the duty cycle does not exceed fifty percent.

An input 68 of computer 52 is coupled to the tap terminal 48 of alternator 34. As the alternator shaft 50 rotates, a sinusoidal signal emanates from tap terminal 48. The peak portions of that signal strobe input 68, generating a hardware interrupt at a frequency equal to the rate of rotation of shaft 50. The computer 52 can time the period between these interrupt signals to calculate the rate of the user's exercise movement.

Control Panel

Figure 3:
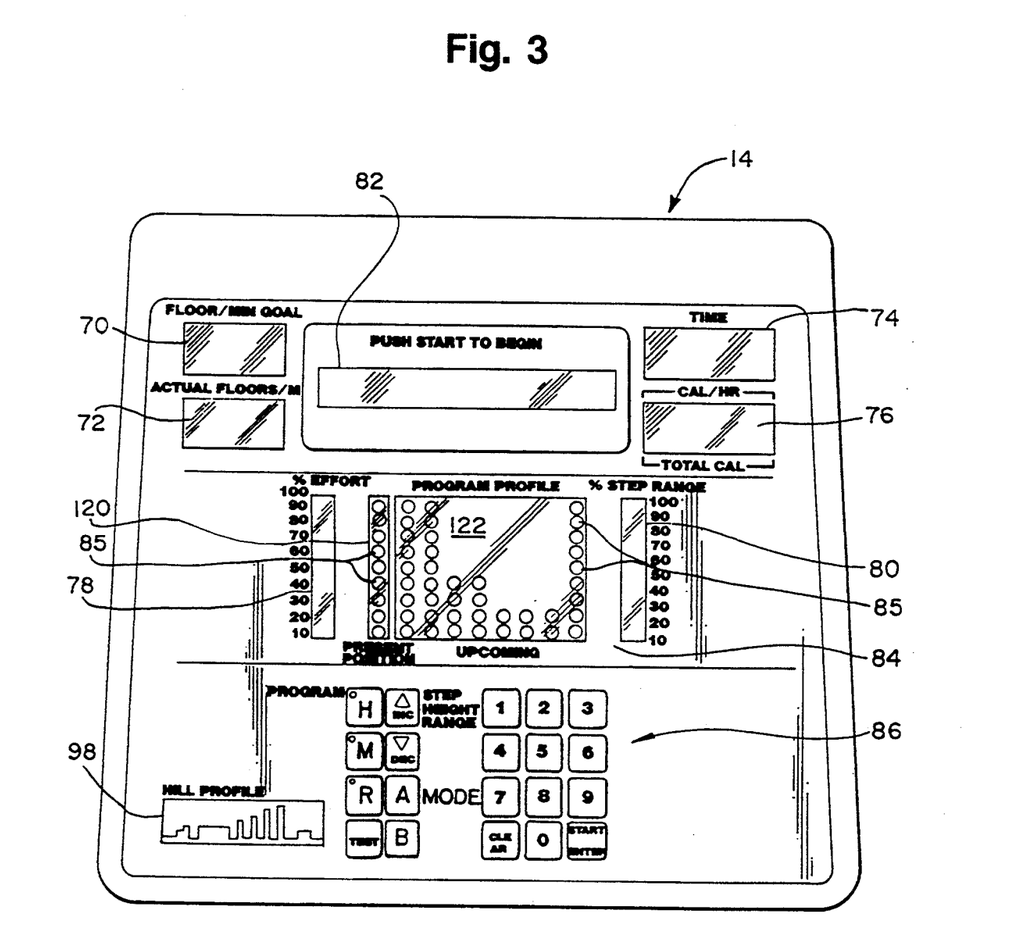
FIG. 3 is a plan view of a control panel that is part of the exercise device illustrated in FIG. 1.

Referring now to FIGS. 2 and 3, it will be seen that computer 54 is linked to the control panel 14 for managing user input-output. The panel 14 includes displays designed to accommodate operation of exercise device 10 in a "regular" and a "climbing" mode, although the invention may be practiced without the regular mode. In the regular mode, the exercise device 10 operates as a conventional system, wherein the user's effort level is controlled by regulating the rate at which the user exercises. To this end, panel 14 includes a display 70 for prompting the user to exercise at a particular rate (expressed in floors per minute), and a display 72 of the user's actual rate of exercise.

The panel 14 includes informational displays 74 and 76 of elapsed time and expended calories, respectively, as well as displays 78 and 80 of percentage of effort and step height, respectively. An alpha-numeric display 82 displays messages to the user including instructions on how to use device 10.

The display 78 is a column of LED's, where the individual LEDs are lit in sequence to indicate to the user the percentage of effort that he or she is expending. In this case, the percentage of effort is the percent the actual rate of exercise bears to the target rate.

The display 80 is also a column of successively lit LEDs which graphically illustrates the percentage which the user's actual displacement of pedal members 16 and 18 bears to a target displacement. The actual displacement may be measured by a position sensor (not shown).

In the climbing mode, the exercise device 10 operates in accordance with the invention. Displays 70, 78 and 80 need not be used because in the climbing mode exercise device 10 does not regulate the user's rate of exercise. Rather, exercise device 10 regulates (independent of exercise rate) the resistance which alternator 34 imparts to the user's reciprocating exercise motion. As discussed below in greater detail, the current and upcoming levels of resistance are displayed in a program profile lamp matrix 84. Matrix 84 includes an array of LEDs 85. For clarity, not every one of LEDs 85 is illustrated in FIG. 3. Alternatively, other sources of illumination such as LCD, for example, may be used.

Panel 14 also includes a keypad 86 which enables the user to select programs, modes, and enter data such as weight. As illustrated in FIG. 3, the keypad 86 includes keys A and B for selecting one of the above-described regular and climbing modes, respectively. Keys H, M and R enable the user to select a program for operation in the selected one of climbing and regular modes. The available exercise programs are Hill, Manual and Random, and are selected by pressing the H, M and R keys, respectively. These programs are described below with respect to the climbing mode.

Periodic update of the information displayed on the panel 14 is performed by the computer 54 using information provided by the computer 52 and transmitted to the computer 52 via the link 56. Keypad 86 is monitored by the computer 54 and, the user's input is transmitted to the computer 52 via the link 56.

Climbing Mode

The invention may be best understood by describing the operation of exercise device 10 in the climbing mode. Initially, the user selects the climbing mode by pressing the B key. Software programs resident in nonvolatile memory 58 of computer 54 are then executed to (i) prompt the user for various data, and (ii) perform an exercise program in accordance with the invention. Alternatively, the user could select the climbing mode after entering data or even during exercise, for example.

Figure 4:
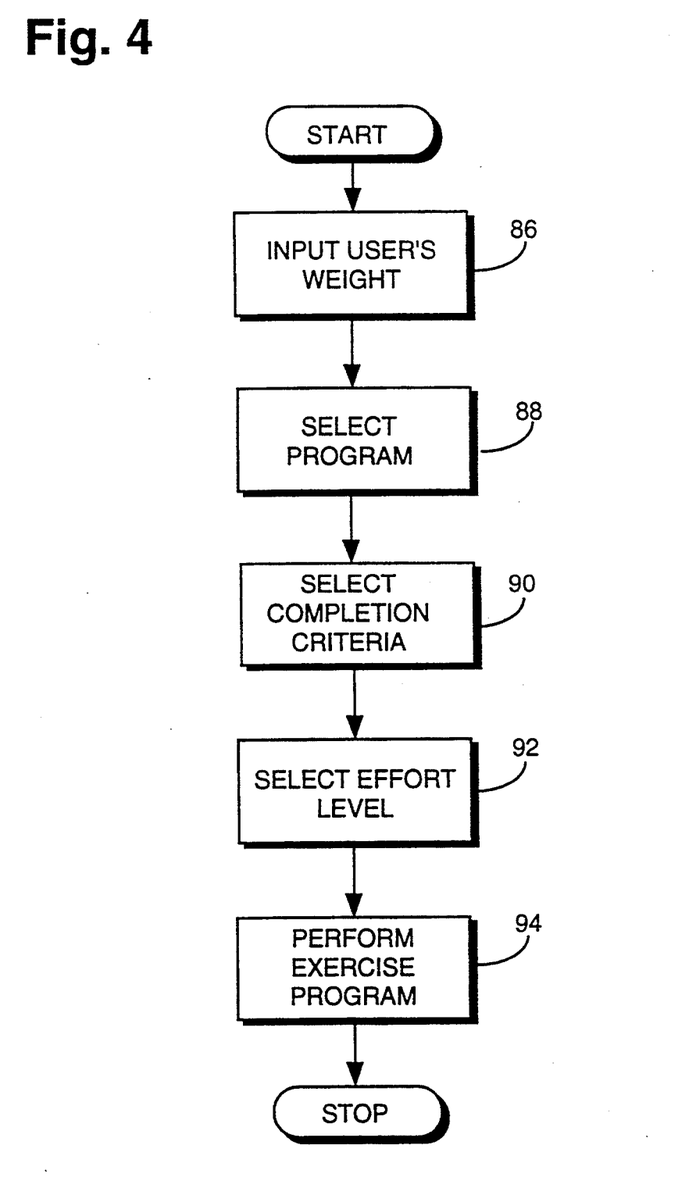
FIGS. 4 and 5 are logic flow charts illustrating the operation of the exercise device shown in FIG. 1.
Figure 5:
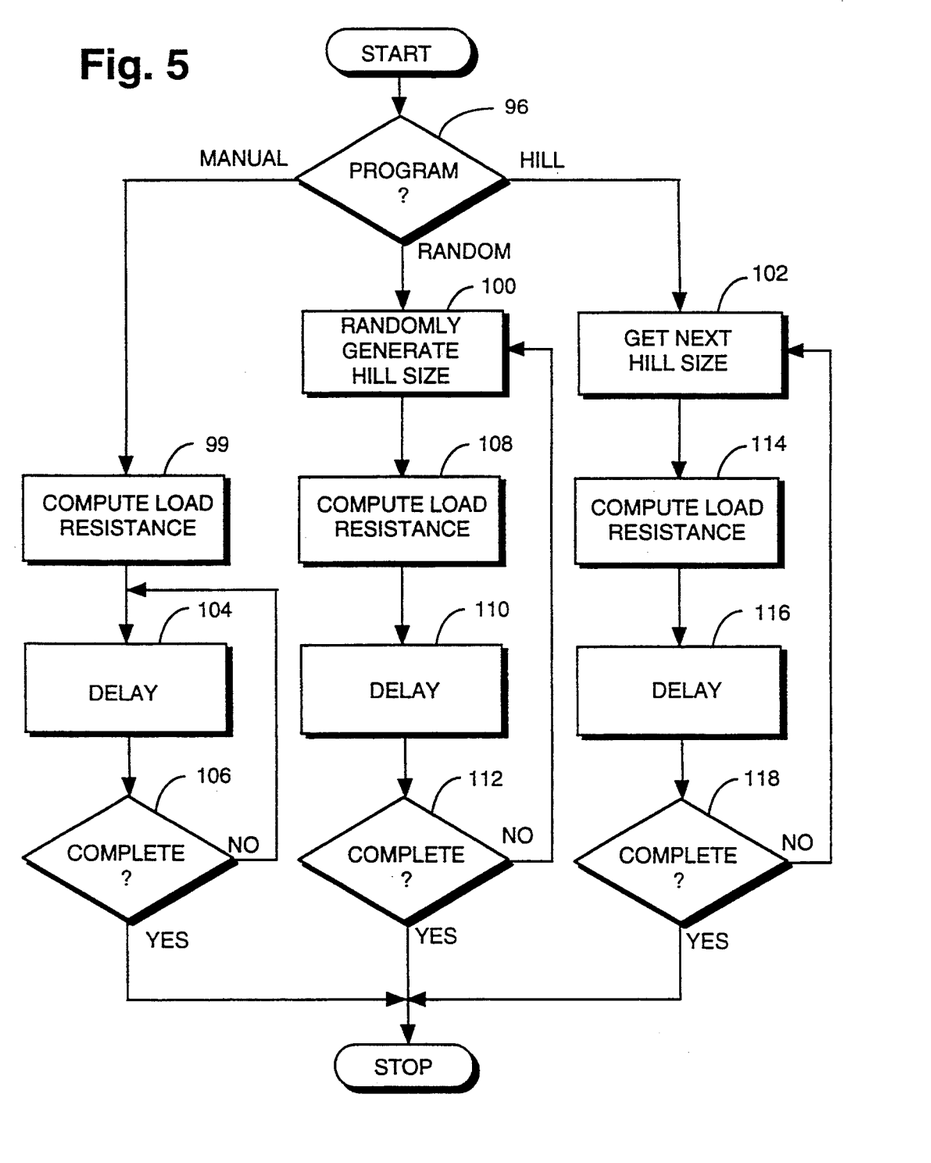

Referring to FIGS. 4 and 5, these software programs are now described. As shown at a block 86 of FIG. 4, computer 54 via panel 14 prompts the user to enter his weight in pounds. At a block 88, the user is prompted to select one of the Hill, Random, and Manual programs by pressing one of the H, R and M keys, respectively.

At a block 90, the user is prompted to enter a completion criteria. The completion criteria establishes the basis for terminating the exercise in the Random and Manual programs. Suitable criteria include the elapsed time of exercise, the amount of calories expended, and the distance (expressed in floors) climbed.

In the case where the completion criteria is the amount of calories consumed, computer 52 calculates the calories consumed by the user on the basis of the load resistance, the distance climbed and the user's weight. Periodically, computer 52 compares the cumulative calories consumed to a user-entered target. When the actual cumulative calories consumed exceeds the target, the computer 52 alerts the user by an alarm, flashing light or other suitable means. Computer 52 can also discontinue load resistance to advise the user that the completion criteria has been reached.

Applicant's climbing mode allows the use of calorie consumption as a completion criteria because, unlike the prior art, the Applicant's climbing mode controls the load resistance during exercise.

At a block 92, the user is prompted to enter an effort level. In the preferred embodiment, there are twelve effort levels of increasing difficulty. Each level is associated with a range of load resistance, and the ranges may be successive or overlapping.

At a block 94, the exercise program is performed until the selected completion criteria is met or, in the case of the Hill Program, a predetermined routine is completed. Referring to FIG. 5, the operation of exercise device 10 at the block 94 is described in greater detail. Beginning at a block 96, computer 52 determines which of the Hill, Random and Manual programs the user has entered.

As discussed above, in accordance with the invention, the exercise device 10 controls load resistance (as opposed to the rate of exercise), allowing the user to step at any desired rate in a more natural simulation of climbing. The resistance is varied in accordance with the selected one of the Hill, Random and Manual programs. In each case program, computer 52 selects one or more numbers (or "difficulty values") that are associated with hill height, size steepness or other indicator of difficulty. The load resistance is a function of these selected values. Thus, the higher the hill difficulty value, the greater the load resistance against the user's exercise movement. For purposes of this specification, the terms "hill height", "hill size" and "hill difficulty" are sometimes used interchangeably. The computer 52 therefore generates a load control signal 60 having a duty cycle that produces a constant resistance corresponding to the selected hill size or climbing difficulty. It is the constant resistance, independent of the rate of exercise, that very effectively provides the user with the sensation of climbing hill having the selected size.

In the Hill program, the hill difficulty values are selected in accordance with a predetermined routine stored in nonvolatile memory 58. This routine is graphically displayed on an indicia 98 affixed to panel 14 (as seen in FIG. 3). The height of the vertical bars depicted in indicia 98 correspond to the amplitude of the load resistance with respect to time, which is represented along the horizontal axis, moving left to right. (The Hill program can also include a number of routines of varying but predetermined time durations.) A legend on the indicia 98 can associate the height of the vertical bars with the concept of hill height or difficulty.

In the Random program, the hill difficulty values are randomly selected from a predefined range by computer 52. In practice, the computer 52 can generate a series of random numbers when exercise begins, and can store the generated numbers in an array for serial retrieval during exercise. Once the random numbers are stored in memory, they become, in effect, a routine such as the predetermined routine invoked during operation of the Hill program.

In the Manual program, the load resistance is maintained at a fixed level of difficulty. Contrastingly, in the Hill and Random programs, the computer 58 successively selects (either randomly or in accordance with a preselected routine) one of (preferably) seven values of hill difficulty.

Referring again to FIG. 4, depending on which program has been selected, control moves from the block 96 to one of the blocks 99, 100, and 102. If the Manual program is selected, the computer 58 computes the load resistance at a block 98. After a delay period at block 104 (which may be of any suitable length such as for example one second) the computer 58 checks the completion criteria at a block 106 to determine if exercise is complete. If exercise is complete, the program terminates. Otherwise, control returns to the block 104, and the iteration of blocks 104 and 106 is repeated until the completion criteria is met.

If the Random program is selected, the computer 52 at a block 100 generates a random number corresponding to hill difficulty value. As mentioned, a series of random numbers may be generated at the same time and stored in an array. In this event, at the block 100 the computer 52 would fetch the next hill difficulty value from the array.

Alternatively, the computer can initially randomly generate a predetermined number of numbers, which are stored FIFO-wise in a circular buffer. With each iteration of the block 100, the earliest generated number is taken from the buffer, and a new randomly generated number is placed into the buffer. In this manner, at least some of the upcoming randomly selected hill difficulty values will be stored in memory for display on the program profile matrix 84, as described below.

The computer 52 then computes the load resistance at a block 108. After a delay period of any suitable length (represented by a block 110), the computer 54 checks the completion criteria at a block 112 to determine if exercise is complete. If exercise is complete, the program terminates. Otherwise, control returns to the block 100, and the iteration of blocks 100 and 108–112 is repeated until the completion criteria is met. In practice, a new difficulty value should be selected only on each Nth iteration or block 100, where N is a number sufficiently large so that the difficulty level does not change too often.

If the Hill program is selected, the computer 52 at a block 102 fetches the next hill difficulty value from the stored routine. The computer 52 then computes the load resistance at a block 114. After a delay period of any suitable length (represented by a block 116), computer 52 determines at block 118 if the predetermined routine is complete. If the preselected routine is complete, exercise terminates. Otherwise, control returns to the block 102, and the iteration of blocks 102 and 114–118 is repeated.

Load resistance as calculated by the computer 52 at the blocks 99, 108 and 114 is expressed as a duty cycle of the control signal 60 generated by the computer 52. Duty cycle is a computed function of the user's weight, the user-selected effort level and the current hill difficulty value (or "size"). In mathematical terms, Duty Cycle = F (weight, effort level, hill size).

In the Manual program, hill size (and, therefore, load resistance) is constant. But in the Hill and Random programs, hill size is varied, thus modulating load resistance over time.

Through empirical testing, a number of formulae have been found that can be used to compute duty cycle as a function of weight (in pounds), effort level and hill size. However, the following formula was found to be particularly effective:

$$K_1 * \{K_2 + weight * weight/K_3 + level * K_4 + [(level * K_5 + K_6)/K_7] * [hill - K_8]\};$$

ps where $K_1$ equals 0.33; $K_2$ equals 19; $K_3$ equals 2500; $K_4$ equals 2; $K_5$ equals 2; $K_6$ equals 30; $K_7$ equals 8; and $K_8$ equals 2. When the highest level is selected, $K_4$ may be set to three to give experienced users a particularly strenuous workout.

The actual values of the foregoing constants should be calibrated for specific embodiments of the invention. Of importance, however, is that the duty cycle be a function of the square of the user's weight. It is believed that the sensation of climbing is more realistic and comfortable when the weight term is thus squared.

The duty cycle as indicated above is generally proportional to the resistance felt by the user as he steps down on the pedals 16 and 26. This duty cycle as indicated by the formula above is computed independently of the user's rate of stepping as indicated by the display 72.

The program profile lamp matrix display 84 successively displays a plurality of images representing hills. Each hill image is associated with a difficulty level, which is graphically represented by the image. Specifically, display 84 indicates present and upcoming hill difficulty values in a matrix of LEDs 85. Each vertical column of matrix 84 contains successively illuminated LEDs 85 which define the image of a single "hill". The difficulty value or "height" of the hill is represented by the number of LEDs 85 that are illuminated in the particular column.

The current hill value is displayed in the far left column 120 (or "primary display"). Moving from left to right, the next N hill values which the user will encounter are displayed in display area 122 (or "secondary display"), where N is the number of remaining columns.

During each iteration of the Hill and Random routines, as a hill difficulty value is selected at the blocks 100 or 102 (as shown in FIG. 5), the selected hill value is displayed in the left-most column as the "current hill" value. Thus, the left-most column provides the user with a graphical, real-time representation of the level of load resistance which he or she is experiencing. The higher the displayed hill difficulty value, the greater the load resistance.

In this manner, the visual association of hill height in combination with the level of load resistance reinforces in the user's mind the connotation of steepness and the sensation of climbing hills. Alternatively, the invention may be practiced with more sophisticated displays, including three-dimensional or life-like video representations of hills.

The next N upcoming hill difficulty values displayed in area 122 are also updated each time a new hill value is selected by computer 52. In the Hill program, the computer 52 retrieves these values from the predetermined program. In the Random program, the computer 52 must generate and store at least N random hill values in advance if they are to be displayed in area 122.

It will be observed that the upcoming hill values appear to scroll from right to left across display area 122, providing further visual reinforcement of the sensation that the user is traversing a hilly terrain.

While the present invention has been described with respect to the preferred embodiment, it is understood that other and further modifications, apart from those shown or suggested herein, may be made within the spirit and scope of the invention as defined in the following claims.

We claim:

1. A climbing exercise apparatus, comprising
   a first and second pedal means pivotally secured to a frame and adapted for providing a user with a vertically reciprocating climbing exercise movement for simulating hill climbing;
   resistance means for applying a variable level of resistance in opposition to said reciprocating climbing exercise movement, said resistance means being selectively adjustable in response to a load control signal for varying the level of resistance representing to at least a portion of hill;
   load control means for generating said load control signal to apply said resistance independently of the rate of said reciprocating climbing exercise movement, wherein said load control signal is effective to maintain said resistance at a constant value for a predetermined difficulty value; and display means for displaying an image representing said resistance of said at least a portion of a hill.

2. The apparatus of claim 1 wherein said display means additionally displaying said predetermined difficulty value.

3. The apparatus of claim 2 wherein said control means includes program means for changing said first difficulty value displayed on said display means to a subsequent difficulty value and for changing said load control signal constant value to a subsequent constant value corresponding to said subsequent difficulty value.

4. A climbing exercise apparatus, comprising a frame;
   a first and second pedal means pivotally secured to said frame and adapted for providing a user with a vertically reciprocating climbing exercise movement for simulating hill climbing;
   selection means for generating a plurality of values;

display means comprising primary display means for successively displaying a plurality of images, each of said images representing at least a portion of a hill that is associated with one of said plurality of values, and each of said images graphically representing said associated values;

resistance means connected by a transmission to said first and second pedal means for applying a variable level of load resistance in opposition to said vertically reciprocating climbing exercise movement, said resistance means being selectively adjustable in response to a load control signal for varying the level of load resistance; and control means for generating said load control signal to apply said load resistance independently of said vertically reciprocating climbing exercise movement and directly as a function of said graphically values, wherein said load control signal is effective to maintain said load resistance at a constant value for a predetermined difficulty value.

5. The apparatus of claim 4 wherein said selection means generates said values independently of the user's rate of vertically reciprocating climbing exercise movement.

6. The apparatus of claim 4 wherein said selection means generates said values in accordance with a predetermined routine.

7. The apparatus of claim 4 wherein said selection means generates said values randomly.

8. The apparatus of claim 4 wherein said display means further comprising secondary display means for simultaneously displaying a plurality of images arranged in a selected order, each of said selected order of said images representing a hill that is associated with one of said plurality of values, and each of said images graphically representing said associated value.

9. The apparatus of claim 4 further comprising data entry means for enabling the user to enter data that includes the user's weight, wherein said control means applies said load resistance as a function of the user's weight.

10. The apparatus of claim 9 wherein said control means varies said load resistance as a function of the square of the user's weight.

11. The apparatus of claim 9 wherein said data further includes a number corresponding to one of a predetermined range of effort levels, wherein said function is:

$$K_1 * \{K_2 + \text{weight} * \text{weight}/K_3 + \text{level} * K_4 +$$
$$[(\text{level} * K_5 + K_6)/K_7] * [\text{hill} - K_8]\};$$

where weight is the user's weight in pounds, level is the user-entered number corresponding to an effort level, and hill is the value graphically represented by display means and $K_1$ through $K_8$ are constants.

12. The apparatus of claim 4 wherein said resistance means is an alternator having a control field and a shaft that is coupled to said transmission; wherein said load control signal is a square wave signal having a duty cycle that is varied as a function of the value graphically represented by said primary display means.

13. The apparatus of claim 12 further comprising data entry means for enabling said user to enter data that includes the user's weight; and wherein said duty cycle is varied as a function of the user's weight as well as said graphically represented value.

14. The apparatus of claim 12 wherein said duty cycle is varied as a function of the square of the user's weight.

15. The apparatus of claim 13 wherein said data further includes a number corresponding to one of a predetermined range of effort levels; wherein said duty cycle is varied as a function of said number as well as said user's weight and said graphically represented value.

16. The apparatus of claim 4 wherein said primary display means graphically represents each of said values as a vertical column, the height of which is proportional to said represented value.

17. The apparatus of claim 16 further comprising an indicia visually accessible to the user which associates said represented value with said height of said vertical column.

18. The apparatus of claim 4 wherein said display means additionally including display means for displaying an image representing said load resistance.

19. A method for use in a climbing exercise apparatus having first and second pedal means pivotally secured to a frame and adapted for providing a user with a vertically reciprocating climbing exercise motion for simulating hill climbing, and means for applying a variable level of resistance to said vertically reciprocating climbing exercise motion, comprising the steps of:

generating a plurality of values from within a predetermined range of values;

successively displaying a plurality of images, each of said images representing a hill that is associated with one of said plurality of values, and each of said images graphically representing said associated values;

applying a level of load resistance in opposition to the user's vertically reciprocating climbing exercise motion that is proportional to said graphically represented value; and generating said load resistance independently of said vertically reciprocating climbing exercise motion and directly as a function of said graphically represented values, wherein said load resistance is effective to maintain at a constant value for a predetermined difficulty value.

20. The method of claim 19 further comprising the step of selecting a number corresponding to one of a predetermined range of effort levels; and generating said load resistance as a function of the square of the user's weight and said graphically represented value.

21. The method of claim 19 further comprising the step of simultaneously displaying a plurality of images arranged in a selected order, each of said images representing at least a portion of a hill that is associated with one of said plurality of values, and each of said images graphically representing said associated value.

* * * * *